United States Patent
Schneider et al.

(10) Patent No.: US 10,300,013 B2
(45) Date of Patent: May 28, 2019

(54) INTRA-AMNIOTIC ADMINISTRATION OF EDI200 FOR THE TREATMENT OF ECTODERMAL DYSPLASIAS

(71) Applicants: EspoirXLHED Sàrl, Cambridge, MA (US); FRIEDRICH-ALEXANDER-UNIVERSITAET ERLANGEN-NUERNBERG, Erlangen (DE)

(72) Inventors: Pascal Schneider, Espalinges (CH); Kenneth M. Huttner, Chestnut Hill, MA (US); Neil Kirby, Andover, MA (US); Holm Schneider, Cambridge, MA (US)

(73) Assignees: EspoirXLHED Sàrl, Geneva (CH); FRIEDRICH-ALEXANDER-UNIVERSITAET ERLANGEN-NUERNBERG, Erlangen (DE)

( * ) Notice: Subject to any disclaimer, the term of this patent is extended or adjusted under 35 U.S.C. 154(b) by 22 days.

(21) Appl. No.: 15/030,502

(22) PCT Filed: Oct. 21, 2014

(86) PCT No.: PCT/US2014/061550
§ 371 (c)(1),
(2) Date: Apr. 19, 2016

(87) PCT Pub. No.: WO2015/061302
PCT Pub. Date: Apr. 30, 2015

(65) Prior Publication Data
US 2016/0271055 A1    Sep. 22, 2016

Related U.S. Application Data

(60) Provisional application No. 61/893,937, filed on Oct. 22, 2013.

(51) Int. Cl.
*A61K 9/00* (2006.01)
*A61K 38/17* (2006.01)
*A61K 38/19* (2006.01)

(52) U.S. Cl.
CPC ............ *A61K 9/0034* (2013.01); *A61K 38/17* (2013.01); *A61K 38/191* (2013.01)

(58) Field of Classification Search
None
See application file for complete search history.

(56) References Cited

U.S. PATENT DOCUMENTS

2005/0152872 A1   7/2005   Gaide et al.
2010/0254984 A1   10/2010   Gaide et al.

FOREIGN PATENT DOCUMENTS

WO    2012158445 A1    11/2012
WO    2014078353 A1    5/2014

OTHER PUBLICATIONS

The press release posted Oct. 2010 and downloaded Jan. 6, 2015 from drugs.com/clinical_trials/edimer-pharmaceuticals-presents-edi200-update-intern . . . 3 pages total. (Year: 2010).*
Schneider et al., J. Biol. Chem. 2001, 276:18819-18827. (Year: 2001).*
Zhang et al., Progress in Natural Science 19; 2009: 1197-1200. (Year: 2009).*
Otis & Brent, Anat Rec. 1954; 120 :33-63. (Year: 1954).*
Gaide and Schneider, Permanent correction of an inherited ectodermal dysplasia with recombinant EDA. Nature Medicine, 2003, 9 (5): 614-618.
Cespedes et al., Steady-State Pharmacokinetics, Cord Blood Concentrations, and Safety of Tionavir-Boosted Fosamprenavir in Pregnancy. J. Acquir Immune Defic Syndr. Apr. 2013, vol. 62(5), p. 550-554.
Bzowej, Optimal Management of the Hepatitis B Patient Who Desires Pregnancy or is Pregnant. Curr Hepat Rep. 2012, vol. 11(2), p. 82-89, p. 82.
Edimer_EDI200, Information for Patients—What is EDI200? Edimer Pharmaceuticals, 2012 [online]. [Retrieved on Dec. 1, 2014].
Edimer_XLHED, XLHED Information for Dentists, Edimer, 2014 [online]. [Retrieved on Dec. 1, 2014].
International Search Report received for corresponding PCT application No. PCT/US2014/061550 dated Jan. 5, 2015.
Holm Schneider et al: "Prenatal therapy in developmental disorders: drug targeting via intra-amniotic injection to treat X-linked hypohidrotic ectodermal dysplasia", Orphanet Journal of Rare Diseases, Biomed Central LTD, LO, vol. 9, No. Suppl 1, Jul. 10, 2014 (Jul. 10, 2014), p. P10.
Kenneth Huttner: "EDI200 therapeutic trial", Head & Face Medicine, Biomed Central, London, GB, vol. 8, No. Suppl 1, May 25, 2012 (May 25, 2012), p. 118.
Anonymous: "Phase 2 Study to Evaluate Safety, Pharmacokinetcs and PHarmacodynamics/Efficacy of EDI200 in Male Infants With X-Linked Hypohidrotic Ectodermal Dysplasia (XLHED)", Jul. 3, 2013 (Jul. 3, 2013).
Extended European Search Report received in corresponding EP Application No. 14856488.3 dated May 8, 2017.

* cited by examiner

*Primary Examiner* — Christina M Borgeest
(74) *Attorney, Agent, or Firm* — Finnegan, Henderson, Farabow, Garrett & Dunner LLP

(57) ABSTRACT

The invention relates to methods for the intra-amniotic administration of EDA agonists, in particular EDI200. Use of the methods described allow for the design of targeted therapeutic dosing and administration regimens in order to correct or alter abnormal phenotypes associated with ectodermal dysplasias, in particular, XLHED.

10 Claims, 6 Drawing Sheets
Specification includes a Sequence Listing.

Starch Iodine test to detect sweat production at the paws:

Footpad sections with eccrine sweat glands (arrows):

SEQUENCE LISTING

```
<160> NUMBER OF SEQ ID NOS: 1

<210> SEQ ID NO 1
<211> LENGTH: 380
<212> TYPE: PRT
<213> ORGANISM: Artificial Sequence
<220> FEATURE:
<223> OTHER INFORMATION: Artificial Sequence: synthetic peptide

<400> SEQUENCE: 1

Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
```

-continued

```
            115                 120                 125
Thr Leu Pro Ser Arg Asp Glu Leu Thr Lys Asn Gln Val Ser Leu
        130                 135                 140
Thr Cys Leu Val Lys Gly Phe Tyr Pro Ser Asp Ile Ala Val Glu Trp
145                 150                 155                 160
Glu Ser Asn Gly Gln Pro Glu Asn Asn Tyr Lys Thr Thr Pro Pro Val
                165                 170                 175
Leu Asp Ser Asp Gly Ser Phe Phe Leu Tyr Ser Lys Leu Thr Val Asp
                180                 185                 190
Lys Ser Arg Trp Gln Gln Gly Asn Val Phe Ser Cys Ser Val Met His
            195                 200                 205
Glu Ala Leu His Asn His Tyr Thr Gln Lys Ser Leu Ser Leu Ser Pro
210                 215                 220
Gly Lys Ala Asp Lys Ala Gly Thr Arg Glu Asn Gln Pro Ala Val Val
225                 230                 235                 240
His Leu Gln Gly Gln Gly Ser Ala Ile Gln Val Lys Asn Asp Leu Ser
                245                 250                 255
Gly Gly Val Leu Asn Asp Trp Ser Arg Ile Thr Met Asn Pro Lys Val
                260                 265                 270
Phe Lys Leu His Pro Arg Ser Gly Glu Leu Glu Val Leu Val Asp Gly
            275                 280                 285
Thr Tyr Phe Ile Tyr Ser Gln Val Glu Val Tyr Tyr Ile Asn Phe Thr
        290                 295                 300
Asp Phe Ala Ser Tyr Glu Val Val Val Asp Glu Lys Pro Phe Leu Gln
305                 310                 315                 320
Cys Thr Arg Ser Ile Glu Thr Gly Lys Thr Asn Tyr Asn Thr Cys Tyr
                325                 330                 335
Thr Ala Gly Val Cys Leu Leu Lys Ala Arg Gln Lys Ile Ala Val Lys
                340                 345                 350
Met Val His Ala Asp Ile Ser Ile Asn Met Ser Lys His Thr Thr Phe
            355                 360                 365
Phe Gly Ala Ile Arg Leu Gly Glu Ala Pro Ala Ser
        370                 375                 380
```

INTRA-AMNIOTIC ADMINISTRATION OF EDI200 FOR THE TREATMENT OF ECTODERMAL DYSPLASIAS

CROSS REFERENCE TO RELATED APPLICATIONS

This application is a 35 U.S.C. § 371 U.S. National Stage Entry of International Application No. PCT/US2014/061550 filed Oct. 21, 2014 which claims priority to U.S. Provisional Patent Application No. 61/893,937, filed Oct. 22, 2013 entitled Intra-Amniotic Administration of Proteins for the Treatment of Ectodermal Dysplasias, the contents of which is incorporated herein by reference in its entirety.

REFERENCE TO SEQUENCE LISTING

The instant application is being filed along with a Sequence Listing in electronic format. The Sequence Listing is provided as a file entitled 2003-1005US371SEQLST.txt, created on Mar. 29, 2016, which is 3,820 bytes in size. The information in the electronic format of the sequence listing is incorporated herein by reference in its entirety.

FIELD OF THE INVENTION

The invention relates to compositions and methods of their use for altering and/or modifying the phenotype of an individual diagnosed with or suspected of having an ectodermal dysplasia such as XLHED by intra-amniotic administration of one or more therapeutic compounds and/or pharmaceutical compositions.

BACKGROUND OF THE INVENTION

Ectodermal embryogenesis contributes to development of the epidermis and associated structures such as sweat glands, sebaceous glands, mammary glands, Meibomian glands, hair follicles and nails. Ectoderm derivatives also include the anterior ⅔ of the oral cavity, and structures including the epithelia of salivary glands, the enamel of teeth, the covering of the tongue, and part of the pituitary gland.

X-linked hypohidrotic ectodermal dysplasia (XLHED) is a rare X chromosome-linked genetic disorder. It is the most common of the ectodermal dysplasias, a spectrum of more than 170 genetic disorders that are characterized by at least one primary morphological defect of ectodermal structures (Pinheiro, M. et al., Am J Med Genet. 1994 Nov. 1; 53(2):153-62, the contents of which are incorporated herein by reference in its entirety). XLHED is clinically characterized by fine, sparse hair (hypotrichosis); few and often pointed teeth (marked oligodontia); diminished or absent eccrine function (hypohidrosis) associated with an elevated risk for life-threatening hyperthermia; and a predisposition to serious, clinically-significant respiratory infections associated with reduced secretory gland function. In addition to humans, the disease has been identified in dogs, mice and cattle.

XLHED is caused by mutations in the EDA gene, chromosomal locus Xq12.q13.1 (Kere, J. et al., Nat Genet. 1996 August; 13(4):409-16). The EDA gene encodes several splice variants, the longest of which encodes the 391 aa. protein EDA-A1 that is a member of the TNF family and binds specifically to its cognate receptor EDAR. Replacement studies in mice and dogs have confirmed that EDA-A1 is the only EDA gene product necessary to activate the EDA/EDAR signaling pathway (Casal, M. L. et al., Am J Hum Genet. 2007 November; 81(5):1050-6; Gaide, O. et al., Nat Med. 2003 May; 9(5):614-8).

The EDA-A1/EDAR pair signals through an adaptor molecule called the ectodysplasin-A receptor associated death domain (EDARADD) and the transcription factor nuclear factor-kappa B (NF-κB) pathway (Elomaa, O. et al., Hum Mol Genet. 2001 Apr. 15; 10(9):953-62; Headon, D. J. et al., Nature. 2001 Dec. 20-27; 414(6866):913-6; Kumar, A. et al., J Biol Chem. 2001 Jan. 26; 276(4):2668-77; Schmidt-Ullrich R, Tobin D J, Lenhard D, Schneider P, Paus R, Scheiderheit C (2006), Development 133: 1045-1057). The interaction of EDA-A1 and EDAR exerts a regulatory role that is tightly associated with epithelial-mesenchymal interactions and pathways that regulate ectodermal appendage formation and organogenesis in the embryo (Laurikkala, J. et al., Dev Biol. 2001 Jan. 15; 229(2):443-55).

Therefore the genotypic incapacity to synthesize functional EDA-A1 protein results in an XLHED phenotype due to defective ectodermal development. EDA-A1 has been shown to be involved in the morphogenesis of hair follicles and tooth buds during early development.

In this disorder, there is significant morbidity and mortality in affected children due to hyperthermia, caused by the inability to sweat. Significant morbidities include increased risk of respiratory tract infections, ocular disease due to dry eyes, as well as difficulties with mastication, growth retardation, poor appearance, and speech impairment resulting from tooth abnormalities (delayed dentition, conical tooth crowns (peg-shaped teeth) and oligodontia). As XLHED is an X chromosome-linked genetic disorder, the clinical phenotype is consistently severe in affected males and more variable in heterozygous females as the result of random X chromosome inactivation.

The first model of XLHED was identified in mice selected from the Black 6 strain for large size which resulted in the spontaneous appearance of a sub-strain with abnormal hair and tooth development. The affected animals (designated "Tabby mice" due to the resemblance of the fur patterning of the heterozygote females to that of the tabby cat) lack functional EDA protein due to a frame-shift mutation resulting in the absence of the domain necessary for receptor binding and signaling that is critical for normal tooth, hair and sweat gland morphogenesis (Ferguson, B. M. et al., Hum Mol Genet. 1997 September; 6(9):1589-94; Srivastava, A. K. et al., Proc Natl Acad Sci USA. 1997 Nov. 25; 94(24):13069-74). Consequently, these mice have no sweat glands and no hair on the tail. The Tabby mouse currently is a widely used model for XLHED.

There is a dog model of the disease that has been used in XLHED studies. A German shepherd puppy was identified with a phenotype similar to human XLHED (Casal, M. L. et al., Mamm Genome. 2005 July; 16(7):524-31), and the effect was later bred into the Beagle strain, which is more commonly used for laboratory experimentation. Beagles carrying the EDA mutation exhibit a phenotype equivalent in many significant respects to that of humans. Advantages of the canine model include high geno-/pheno-copy and a dose similarity to human developmental maturation at birth, while disadvantages include the minimal transplacental immunoglobulin transport.

Given the severity of the phenotypic manifestations of XLHED including hyperthermia and respiratory tract infections in the first years of life, followed by significant and life-long health and quality of life issues, there remains a long-felt need for treatment interventions at every stage of life. To date, there is no satisfactory treatment that has been approved for patients affected by XLHED.

Until recently, correction, alteration and/or mitigation of the phenotypic presentations associated with XLHED in animal models has been accomplished by the administration of a recombinant form of the ligand for the EDA receptor. Such recombinant compositions previously identified include those described in detail in U.S. patent application Ser. No. 12/756,268 filed Apr. 8, 2010 which is a continuation of U.S. patent application Ser. No. 10/503,999 filed Oct. 25, 2004, now granted U.S. Pat. No. 7,736,657, which is a 35 U.S.C. Section 371 National Phase Entry Application of International Application No. PCT/EP2002/009354 filed Aug. 21, 2002, which designates the U.S., and which claims the benefit of priority of German Application No. 10205368.5 filed Feb. 10, 2002 and German Application No. 10205583.1 filed Feb. 11, 2002, the contents of which are each incorporated herein by reference in their entireties.

Administration to the fetus of such recombinant compositions has, until now, been effected only via administration to the mother via an intravenous route. Such studies are disclosed in co-pending and commonly owned International Application PCT/US2012/037251 filed May 10, 2012, the contents of which are incorporated herein by reference in their entirety. In Tabby mice prenatal EDA1 replacement via maternal injection of EDI200 corrected the developmental abnormalities to a far greater extent than postnatal administration to newborn pups.

This approach, however, may not be optimal for achieving therapeutic levels of corrective protein in a human fetus and additionally exposes the mother to high serum levels of the exogenous molecule. The inventors hypothesize that direct injection of EDI200 into the amniotic fluid could result in fetal uptake, possibly via gut and lung, leading to a prolonged drug exposure at levels sufficient for successful treatment of XLHED.

The present invention provides compositions and methods for the correction and/or reversal of ectodermal dysplasia, in particular XLHED, phenotypes through direct intra-amniotic administration of recombinant amino-acid based compounds and compositions which comprise EDI200 monomers, multimers, variants, fragments and/or combinations of the foregoing.

SUMMARY OF THE INVENTION

In some embodiments the present invention is directed to a method for altering one or more phenotypic presentations of ectodermal dysplasia in a mammalian organism diagnosed with or suspected of having ectodermal dysplasia comprising, administering to said mammalian organism a pharmaceutical composition comprising proteins which alter cell signaling and wherein administration is via an intra-amniotic route.

Such methods have utility in the treatment and/or amelioration of any of the ectodermal dysplasias. In one embodiment the ectodermal dysplasia is hypohydrotic ectodermal dysplasia.

In some embodiments intra-amniotic administration is effected via direct injection into the amniotic sac or via catheter infusion to the amniotic sac.

In some embodiments the mammalian organism is a human fetus and the pharmaceutical composition is administered at a time period during gestation selected from the group consisting of the second trimester and the third trimester of pregnancy.

In some embodiments, the pharmaceutical composition is administered in a dose of between 1 mg/kg and 100 mg/kg of fetal weight.

Figure 4A:
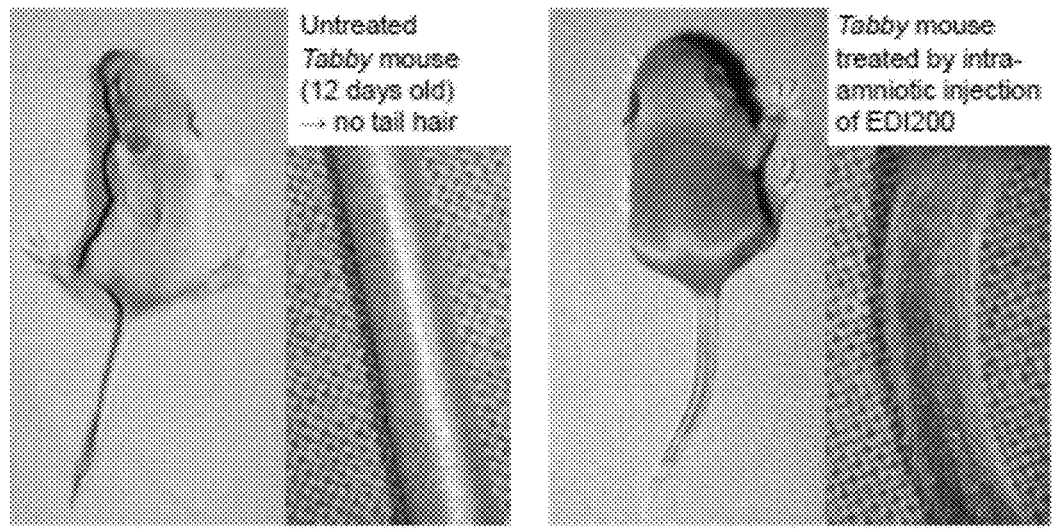
Figure 4B:
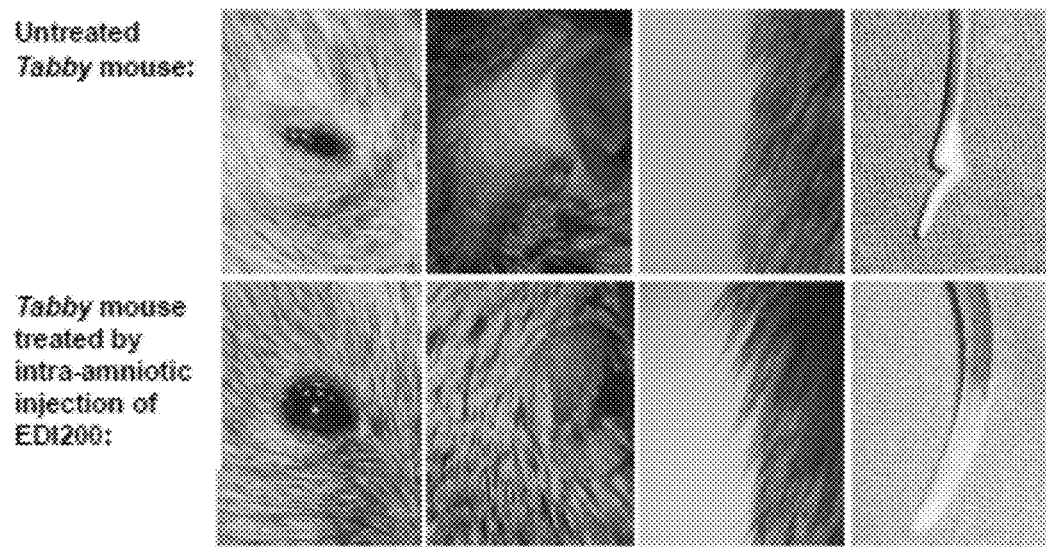

A panel of photographs taken of treated and untreated Tabby mice is shown in FIG. 4A: that Tabby mouse fetuses treated with EDI200 were born without complications and showed normal weight gain and darker coat than untreated control animals and in FIG. 4B: that eyes were more open hair was more plentiful in the retroauricular region; guard hair and tail hair were also normal; and tail tip was normal. In contrast to a single maternal injection of EDI200 in Tabby mice at E15, which corrected the XLHED phenotype in offspring only partially, a single intra-amniotic dose of 10 mg/kg or above resulted in compete phenotypic correction. No adverse effects were observed. All treated Tabby mice showed normal behavior and fertility.

Figure 5A:
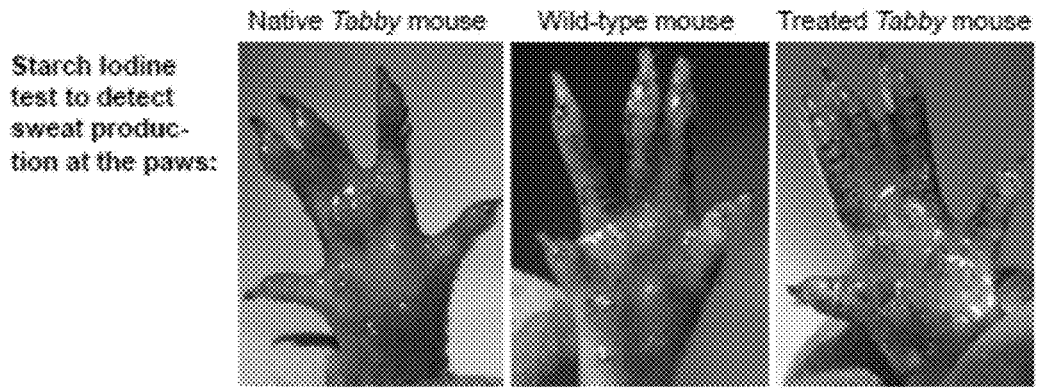
Figure 5B:
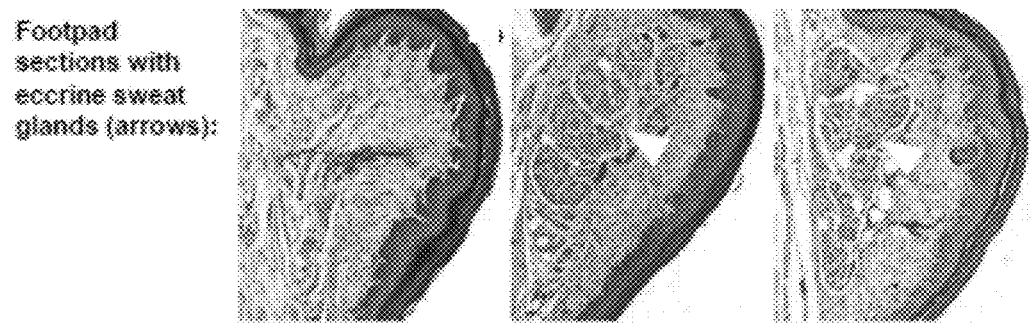

FIG. 5A and FIG. 5B are a panel of photographs taken of wild-type, treated and untreated Tabby mice demonstrating that EDI200 restores the presence (FIG. 5B) and function (FIG. 5A) of sweat glands in the footpads of treated fetuses.

Figure 6:
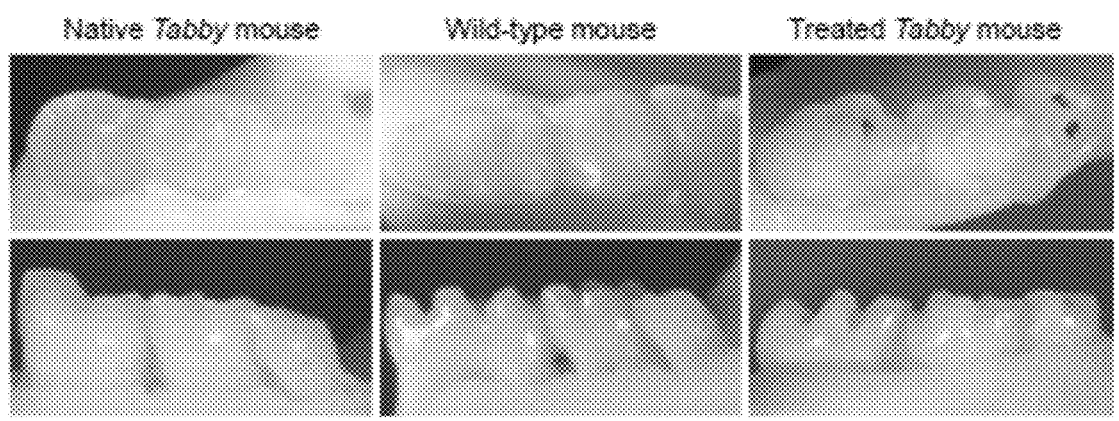

FIG. 6 is a panel of photographs taken of treated, untreated and wild type mice. The photographs illustrate that administration of EDI200 via intra-amniotic route at E15 reverses the Tabby tooth phenotype as evidenced by the clearly defined dentition of the molars.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of methods featured in the invention, suitable methods and materials are described below. During pregnancy nutrients and vital proteins, antibodies in particular, routinely pass from the blood of the mother to the amniotic fluid of the developing fetus. Many studies have shown that drugs are capable of crossing the placental barrier following maternal intravenous injection. However, transfer of proteins from mother to fetus is variable, titer in maternal plasma is most often higher and or equal to fetal concentration (Audus, K. L. (1999) Eur. J. Pharm. Sci. 8, 161-165). In addition, blood has a very narrow pH range from 7.35-7.45, while amniotic fluid has a more neutral range from 7-7.5 (Losch et al. BJOG. 2003 May; 110(5): 453-6).

According to the present invention, delivery of EDI200 by intra-amniotic injection reduces variability in effective dose as well as avoids excessive exposure to the mother. EDI200 drug delivery may also deliver improved pharmacokinetics due to amniotic recycling, swallowing and excretion of amniotic fluid (Ross et al. Am J Physiol. (1998) April; 274 R879-93).

Immune privilege is a system of localized immunosuppression in specific tissues, such as the eye, testes, and placenta, where normal immune functions, such as inflammation, would not be beneficial. A human fetus presents with a genetic mixture of paternal and maternal DNA, a composition that makes the fetus both 'self' and 'non-self' in relation to the mother. The immune system normally reacts to 'non-self' signals by the initiation of inflammation followed by cell-based immune defense, including T-cells and B-cell antibody generation. Amniotic fluid is an immune-privileged site that contains many immunosuppressive molecules to prevent inflammation and also lacks drainage to the lymph nodes, the first step in generating a cell based immune response. (Hunt, Immunol Rev. (2006) October; 213: 36-47). In some embodiments, direct injection of EDI200 to the immune-privileged amniotic fluid effectively avoids the problems of induced inflammation and the adaptive immune response that leads to drug immunogenicity.

According to the present invention, methods are provided for the intra-amniotic administration of pharmaceutical compositions for the treatment of ectodermal dysplasias, in particular XLHED.

The development of different EDA-dependent structures can be induced at distinct time points, and may require different doses or exposure time. Interestingly, some structures can be induced up to several days after their normal development time. This property is of interest when considering EDAR agonists for therapeutic purposes.

In one embodiment, the recombinant form of the ligand EDA-A1 comprising the extracellular domain of the protein fused to a portion of an immunoglobulin (EDI200) is used to correct phenotype abnormalities in the mammalian fetus. EDI200 is a fully humanized Fc fusion protein consisting of the Fc region of human IgG1 and the receptor binding domain (Tumor Necrosis Factor (TNF) domain) of EDA-A1. The biologically active species is glycosylated and exists primarily as a hexamer, comprised of six identical Fc:EDA-A1 monomeric species. The 380 amino acid sequence of the monomeric species is provided herein as SEQ ID NO: 1. EDI200 contains the receptor binding domain of the normally active form required for EDA signaling. As a control, EDAR-Fc, a recombinant protein consisting of the extracellular domain of the EDA receptor fused to the Fc portion of an immunoglobulin, can be used as an inhibitor of EDI200 in order to control the duration of EDI200 activity in vivo.

It has previously been demonstrated that there exists a time course of EDA receptor (EDAR) expression in mammals and that there are unique windows of efficacy for administration of EDI200 in order to at least partially correct abnormal phenotypes associated with the absence of EDA signaling such as those seen in patients with XLHED (International Application PCT/US2012/037251, the contents of which are incorporated herein by reference in their entirety).

It has now been determined that direct intra-amniotic injection results in unexpectedly superior phenotypic outcomes with, in certain phenotypic presentations, a complete restoration of the wild-type phenotype.

Definitions

For convenience, the meaning of certain terms and phrases employed in the specification, examples, and appended claims are provided below. The definitions are not meant to be limiting in nature and serve to provide a clearer understanding of certain aspects of the present invention.

The term "activation" as used herein refers to any alteration of a signaling pathway or biological response including, for example, increases above basal levels, restoration to basal levels from an inhibited state, and stimulation of the pathway above basal levels.

The term "aligned development window" means the correlative timeframes between two or more species in their development of a phenotype. Aligned development windows may reflect treatment windows where the development of two species is in concordance. Aligned development windows may also provide the basis on which to define "leading", "delayed" or "expanded" treatment windows. Use of the term "aligned" herein is not meant to imply that the start and stop points of the windows match exactly. One of skill in the art appreciates that development between any two organisms (even of the same species) will not occur in exactly the same way at exactly the same time. Therefore, it is appreciated that intra- and inter-species variations do occur and that "aligned" is meant to refer to those aligned developmental windows (inclusive of the slight variations) accepted by one of skill in the art.

The term "biological sample" or "biologic sample" refers to a sample obtained from an organism (e.g., a human patient) or from components (e.g., cells) or from body fluids (e.g., blood, serum, sputum, urine, amniotic fluid, etc) of an organism. The sample may be of any biological tissue, organ, organ system or fluid. The sample may be a "clinical sample" which is a sample derived from a patient. Such samples include, but are not limited to, sputum, blood, blood cells (e.g., white cells), amniotic fluid, plasma, semen, bone marrow, and tissue or core, fine or punch needle biopsy samples, urine, peritoneal fluid, and pleural fluid, or cells therefrom. Biological samples may also include sections of tissues such as frozen sections taken for histological purposes. A biological sample may also be referred to as a "patient sample." The patient may be the mother or the fetus.

The term "correlate" or "correlation" as used herein refers to a relationship between two or more random variables or observed data values. A correlation may be statistical if, upon analysis by statistical means or tests, the relationship is found to satisfy the threshold of significance of the statistical test used.

A "development window" is a timeframe for which one or more phenotypes normally develop in an organism. In humans, a developmental window may comprise any of the three trimesters of pregnancy, where the first trimester is between weeks 1-12, the second trimester is between weeks 13-28 and the third trimester is between weeks 29-40 of gestation. It should be understood that in some cases the third trimester may extend to week 42 where a baby is overdue.

The term "embryo" or "fetus" means an unborn offspring in the process of development.

The term "embryonic stage" or "fetal stage" refers to any of the phases through which an embryo passes in development. Embryonic stages have been classified by several methods including the Carnegie stage system and the Theiler stage system.

The term "cell type" refers to a cell from a given source (e.g., a tissue, organ) or a cell in a given state of differentiation, or a cell associated with a given pathology or genetic makeup.

The term "condition" refers to the status of any cell, organ, organ system or organism. Conditions may reflect a disease state or simply the physiologic presentation or situation of an entity. Conditions may be characterized as phenotypic conditions such as the macroscopic presentation of a disease or genotypic conditions such as the underlying gene or protein expression profiles associated with the condition. Conditions may be benign or malignant.

The term "detectable" refers to an RNA expression pattern which is detectable via the standard techniques of polymerase chain reaction (PCR), reverse transcriptase-(RT) PCR, differential display, and Northern analyses, or any method which is well known to those of skill in the art. Similarly, protein expression patterns may be "detected" via standard techniques such as Western blots.

"Mammal" for purposes of treatment refers to any animal classified as a mammal, including humans, domestic and farm animals, and zoo, sports, or pet animals, such as dogs, horses, cats, cows, monkeys etc. Preferably, the mammal is a human.

The phrase "a method of treating" or its equivalent, when applied to, for example, XLHED refers to a procedure or course of action that is designed to reduce, eliminate or alter the phenotypic presentation and/or side effects associated with a disease or condition in an individual, or to alleviate the symptoms of said disease or condition. "A method of treating" a disease or disorder does not necessarily mean that the disease or disorder other disorder will, in fact, be completely eliminated, or that the symptoms of the disease or other disorder will, in fact, be completely alleviated. Often, a method of treating cancer will be performed even with a low likelihood of success, but which, given the medical history and estimated survival expectancy of an individual, is nevertheless deemed an overall beneficial course of action.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

The term "prenatal" means before birth or during pregnancy.

The term "postnatal" means after birth.

The term "phenotypic presentation" refers to the macroscopic presentation of a disease.

The term "predicting" means a statement or claim that a particular event will, or is very likely to, occur in the future.

The term "prognosing" means a statement or claim that a particular biologic event will, or is very likely to, occur in the future.

The term "progression" or "disease progression" means the advancement or worsening of or toward a disease or condition.

The term "subject" refers to patients of human or other vertebrates in particular mammal and includes any individual it is desired to examine or treat using the methods according to the present invention. However, it will be understood that "patient" does not automatically imply that symptoms or diseases are present. As used herein, the term "patient" preferably refers to a human in need of treatment.

The term "treating" as used herein, unless otherwise indicated, means reversing, alleviating, inhibiting the progress of, or preventing, either partially or completely, the phenotypic manifestations of a disease or condition. The term "treatment" as used herein, unless otherwise indicated, refers to the act of treating.

The term "treatment outcome" means the result of one or more treatments. Treatment outcomes may be positive or negative. The nature of the treatment outcome, such as a "positive" outcome may be objectively or subjectively measured. For example, a positive outcome may be reflected in the subjective characterization of the patient of their condition (e.g., the "feel" better), or it may be represented by an objective measurement of the disorder (e.g., an increase in hair growth, tooth morphology or ability to sweat).

The term "treatment window" as used herein refers to the timeframe within which intra-amniotic administration of a pharmaceutical composition will exert at least some positive treatment outcome. Treatment windows may be measured in hours, days, weeks, months or years. They may also occur at a time just after fertilization but prior to embryo implantation, when the organism is in utero or at any time prior to birth. Treatment windows may coincide with "aligned development windows." Treatment windows may be leading, delayed or expanded.

The term "expanded treatment window" means a timeframe during which intra-amniotic treatment may be administered that is longer in duration than a treatment window based solely on an aligned development window. Expanded treatment windows may begin or end coincident with the beginning or ending of an aligned development window and extend either earlier or later in time. They may also be longer than an aligned development window and extend both earlier and later in time, thereby being inclusive of one or more aligned development windows. Expanded treatment windows may be expressed in terms of hours, days, weeks, months or years. Expanded treatment windows may be 1-20%, 2-30%, 5-50% or more longer than the normal development window constituting the aligned development window. They may be 3×, 4×, 5× or more longer.

The term "delayed treatment window" means a timeframe during which intra-amniotic treatment may be administered that begins later in time later than a treatment window based solely on an aligned development window. Delayed treatment windows begin at some time point after an expected aligned development window and extend later in time. They may extend indefinitely and may cover one or more subsequent aligned development windows. Delayed treatment windows may be expressed in terms of hours, days, weeks, months or years. Delayed treatment windows may be 1-20%, 2-30%, 5-50% or more longer than the nonnal development window constituting the aligned development window. They may be 3×, 4×, 5× or more longer. If they are longer than an aligned development window, then by definition the delayed treatment window is an expanded treatment window that simply starts at a later time.

The term "leading treatment window" means a timeframe during which intra-amniotic treatment may be administered that begins earlier in time than a treatment window based solely on an aligned development window. Leading treatment windows begin prior to the beginning of an expected aligned development window. They may also be longer than an aligned development window and extend into and beyond one or more aligned development windows. Leading treatment windows may be expressed in terms of hours, days, weeks, months or years. Leading treatment windows may be 1-20%, 2-30%, 5-50% or more longer than the normal development window constituting the aligned development window. They may be 3×, 4×, 5× or more longer. If they are longer than an aligned development window, then by definition the leading treatment window is an expanded treatment window that simply starts at an earlier time.

The term "therapeutically effective agent" means a composition that will elicit the biological or medical response of a tissue, organ, system, organism, animal or human that is being sought by the researcher, veterinarian, medical doctor or other clinician.

The term "therapeutically effective amount" or "effective amount" means the amount of the subject compound or combination that will elicit the biological or medical response of a tissue, organ, system, organism, animal or human that is being sought by the researcher, veterinarian, medical doctor or other clinician. In this context, a biological or medical response includes treatment outcomes.

Alteration or Modification of Phenotypic Presentation

The present invention provides methods for the correction, alteration or mitigation of various phenotypic presentations associated with ectodermal dysplasia, specifically XLHED, by the intra-amniotic administration of one or more proteins. Phenotypic presentations of ectodermal dysplasias include, but are not limited to, missing or abnormally shaped teeth (including, but not limited to, any of the first, second or third molars, or the first or second premolar, canine or first or second incisors), abnormal morphology or lack of sweat glands, Meibomian glands, glands of the upper respiratory tract, sebaceous glands, salivary glands and other glands, lack or abnormal morphology of various types of hair, and alopecia.

Correction, alteration and/or mitigation of the phenotypic presentations associated with XLHED are accomplished by the intra-amniotic administration of a recombinant form of the ligand for the EDA receptor. Such recombinant EDA compositions include those described in detail in U.S. patent application Ser. No. 12/756,268 filed Apr. 8, 2010 which is a continuation of U.S. patent application Ser. No. 10/503,999 filed Oct. 25, 2004, now granted U.S. Pat. No. 7,736,657, which is a 35 U.S.C. Section 371 National Phase Entry Application of International Application No. PCT/EP2002/009354 filed Aug. 21, 2002, which designates the U.S., and which claims the benefit of priority of German Application No. 10205368.5 filed Feb. 10, 2002 and German Application No. 10205583.1 filed Feb. 11, 2002, the contents of which are incorporated herein by reference in their entireties.

In one embodiment of the invention, the recombinant fusion protein is EDI200. EDI200 is a fully humanized Fc fusion protein consisting of the Fc region of human IgG1 and the receptor binding domain (Tumor Necrosis Factor (TNF) domain) of EDA-A1. The biologically active species is glycosylated and exists primarily as a hexamer, comprised of six identical Fc:EDA-A1 monomeric species. The 380 amino acid sequence of the monomeric species is provided herein as SEQ ID NO: 1.

Administration and Dosing

When the organism to be treated is a mammal such as a human, particularly a human embryo or fetus, the composition may be administered by intra-amniotic methods which may be by a single injection or by infusion using a catheter or any in-dwelling device or pump.

In general, a suitable dose of EDI200 will be in the range of 0.01 to 200.0 milligrams per kilogram body weight of the recipient, patient or individual per day, generally in the range of 1 to 50 mg per kilogram body weight per day. For example, EDI200 can be administered at 0.05 mg/kg, 0.5 mg/kg, 1 mg/kg, 1.5 mg/kg, 2 mg/kg, 3 mg/kg, 3.5 mg/kg, 7 mg/kg, 10 mg/kg, 20 mg/kg, 30 mg/kg, 40 mg/kg, or 50 mg/kg per single dose.

The pharmaceutical composition may be administered, for example to the amniotic fluid, once daily, or may be administered as two, three, or more sub-doses at appropriate intervals throughout the day or even using continuous infusion or delivery through a controlled release formulation. In that case, EDI200 contained in each sub-dose must be correspondingly smaller in order to achieve the total daily dosage. Dosing may also be according to multi-dosing schemes of one, two, three or more doses. The dosage unit can also be compounded for delivery over several days, e.g., using a conventional sustained release formulation which provides sustained release over a several day period. Sustained release formulations are well known in the art and are particularly useful for delivery of agents at a particular site, such as could be used with the agents of the present invention. In this embodiment, the dosage unit contains a corresponding multiple of the daily dose.

The effect of a single dose on any particular phenotype or symptom can be long lasting, such that subsequent doses are administered at not more than 3, 4, or 5 day intervals, or at not more than 1, 2, 3, or 4 week intervals. While administration via the present invention comprises intra-amniotic administration, subsequent administrations may occur after birth.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual pharmaceutical compositions encompassed by the invention can be made using conventional methodologies or on the basis of in vivo testing using an appropriate animal model.

The present invention also includes pharmaceutical compositions and formulations that include the EDI200 compounds featured in the invention. The present invention also contemplates the use of combinations of compounds or combinations of treatment regimens, each of which have as a component intra-amniotic administration of a pharmaceutical composition comprising EDI200. Intra-amniotic administration may result in treatment which is either local or systemic to the embryo or fetus (e.g., unborn baby). Administration to the fetus may be topical or epidermal or transdermal (e.g., by direct contact with the amniotic fluid to which the pharmaceutical composition has been administered), pulmonary, e.g., by inhalation or insufflation; intratracheal, intranasal, or oral of the pharmaceutical composition via fetal respiration. EDI200 can be delivered in a manner to target a particular tissue.

Suitable topical formulations include those in which EDI200 is in an admixture with a topical delivery agent such as lipids, liposomes, fatty acids, fatty acid esters, steroids, chelating agents and surfactants.

In one embodiment of the invention, the subject, patient or individual receiving treatment with a pharmaceutical composition comprising EDI200 is a fetus expressing the abnormal phenotype. In this instance, the fetus may be treated at any time post-conception (fertilization). In one embodiment of the invention, the subject, patient or individual receiving treatment with a pharmaceutical composition comprising EDI200 is a fetus whose genetic status as a carrier of a mutation is unknown but whose mother's status is known.

In one embodiment, the mother is treated within 3 days of fertilization. In another embodiment, the subject or fetus is treated prior to implantation of the embryo. In one embodiment the mother is treated after implantation of the embryo. The mother may be treated at any time during gestation of the embryo. Treatment may be continuous over a number of hours, days or weeks. Treatment may be discontinuous or intermittent. If treated during gestation of her embryo, treatment may be during one or more specified Carnegie stages of her embryo, either sequential or separated, in time.

In one embodiment, the mother is contacted intra-amniotically with a pharmaceutical composition comprising EDI200 at one or more times within Carnegie stages 17-23. In one embodiment, the mother is treated intra-amniotically between Carnegie stage 17 and 22. In one embodiment, the mother is treated intra-amniotically during one of Carnegie stages, 17, 18, 19, 20, 21, 22 or 23. Intra-amniotic treatment may also span one or more stages in whole or in part.

Determination of the treatment window for humans may be accomplished via correlative data from one or more representative animal models where developmental stages have been aligned. Such alignments accepted in the art are those of the Carnegie and Thieler stages. Furthermore and according to the present invention, the range of such aligned treatment widows may vary. Variations may be based on other evidence of developmental process differences known in the art. For example, should a phenotype have been shown to be rescued outside of an aligned development window, the treatment window may be adjusted to account for these data. In one example, it is known that tail hair initiation in the mouse can still take place 4 days after normal development when animals were treated with EDI200. In such a case, the treatment window would coincide with a later Carnegie or Theiler stage and hence be a delayed or enlarged treatment window. Therefore, it should be understood that according to the present invention, treatment windows may be augmented by differences in development such that treatment may be necessary prior to the normal development process of the phenotype in question, after the normal development process of the phenotype in question or along a dosing schedule that is expanded to embrace more than a single development window or aligned development window.

Determination of the intra-amniotic treatment window available to the mother which will alter or modify an abnormal phenotype in the birthed offspring can be made by measuring markers in the pregnant mothers blood or serum which provide correlations to the age of the embryo. Such measurements include, but are not limited to, human chorionic gonadotropin (hCG), hormones such as estrogen, testosterone, progesterone, other bio-indicators of the mother or fetus' status including glucose, proteins and the like. Physical measurements of the embryo or fetus may also inform the appropriate treatment windows. These measurements have the advantage of being non-invasive yet precise. Once such method includes fetal measurements obtained via ultrasound.

It remains the case that should the embryo or fetus require treatment with the compositions of the present invention, such as EDI200, methods are available to deliver the compositions directly to the embryo via endoscopic, surgical or micro-surgical techniques, all via the amniotic sac, hence intra-amniotic. Delivery by such methods may be to a cell, tissue, organ or organ system of the fetus or to the amniotic fluid surrounding the fetus.

The present invention also provides for the treatment of the offspring after birth and after at least one intra-amniotic administration. Depending on the phenotype to be altered, certain treatment windows remain open after birth.

In one embodiment, where tooth morphology presents as abnormal, later treatment with pharmaceutical compositions comprising EDI200 is possible.

Human Embryo Stages

Across the first 60 days of human gestation, 23 distinct morphological "Carnegie" stages (so named because the work was begun at the Carnegie Institution) have been identified based on averages of such features as number of somites, and embryonic length. An embryo is assigned a Carnegie stage (numbered from 1 to 23) based on its external features. Stages are based on the external and/or internal morphological development of the vertebrate embryo, and are not directly dependent on either age or size. The human embryonic period proper is divided into 23 Carnegie stages. These are summarized in Table 1.

TABLE 1

Carnegie Stages of Human Embryo Development

| Stage | Days | Size (mm) | Events |
| --- | --- | --- | --- |
| 1 | 1 | 0.1-0.15 | fertilized oocyte, pronuclei |
| 2 | 2-3 | 0.1-0.2 | cell division with reduction in cytoplasmic volume, formation of inner and outer cell mass |
| 3 | 4-5 | 0.1-0.2 | loss of zona pellucida, free blastocyst |
| 4 | 5-6 | 0.1-0.2 | attaching blastocyst |
| 5 | 7-12 | 0.1-0.2 | implantation |
| 6 | 13-15 | 0.2 | extraembryonic mesoderm, primitive streak |
| 7 | 15-17 | 0.4 | gastrulation, notochordal process |
| 8 | 17-19 | 1.0-1.5 | primitive pit, notochordal canal |
| 9 | 19-21 | 1.5-2.5 | Somite Number 1-3 neural folds, cardiac primordium, head fold |
| 10 | 22-23 | 2-3.5 | Somite Number 4-12 neural fold fuses |
| 11 | 23-26 | 2.5-4.5 | Somite Number 13-20 rostral neuropore closes |
| 12 | 26-30 | 3-5 | Somite Number 21-29 caudal neuropore closes |
| 13 | 28-32 | 4-6 | Somite Number 30 leg buds, lens placode, pharyngeal arches |
| 14 | 31-35 | 5-7 | lens pit, optic cup |
| 15 | 35-38 | 7-9 | lens vesicle, nasal pit, hand plate |
| 16 | 37-42 | 8-11 | nasal pits moved ventrally, auricular hillocks, foot plate |
| 17 | 42-44 | 11-14 | finger rays |
| 18 | 44-48 | 13-17 | ossification commences |
| 19 | 48-51 | 16-18 | straightening of trunk |
| 20 | 51-53 | 18-22 | upper limbs longer and bent at elbow |
| 21 | 53-54 | 22-24 | hands and feet turned inward |
| 22 | 54-56 | 23-28 | eyelids, external ears |
| 23 | 56-60 | 27-31 | rounded head, body and limbs |

Mouse Embryo Stages

Mouse embryos can be staged according to a variety of criteria, the most general of which are those described by Theiler in "The House Mouse: Atlas of Mouse Development" (Springer-Verlag, New York, 1989). The data in Table 2 refer to embryos of crosses between F1 hybrid (C57BL X CBA) mice. The table was excerpted from the EMAP eMouse Atlas Project (emouseatlas.org). The column "dpc" represents days post conception, with the morning after the vaginal plug is found being designated 0.5 dpc (or E0.5).

TABLE 2

Theiler Stages of Mouse Embryo Development

| Theiler Stage | dpc | (C57BLxCBA) F1 mice |
|---|---|---|
| 1 | 0-0.9 | One-cell egg |
| 2 | 1 | Dividing egg |
| 3 | 2 | Morula |
| 4 | 3 | Blastocyst, Inner cell mass apparent |
| 5 | 4 | Blastocyst (zona-free) |
| 6 | 4.5 | Attachment of blastocyst, primary endoderm covers blastocoelic surface of inner cell mass |
| 7 | 5 | Implantation and formation of egg cylinder Ectoplacental cone appears, enlarged epiblast, primary endoderm lines mural trophectoderm |
| 8 | 6 | Differentiation of egg cylinder. Implantation sites 2 × 3 mm Ectoplacental cone region invaded by maternal blood, Reichert's membrane and proamniotic cavity form |
| 9a | 6.5 | Pre-streak (PS), advanced endometrial reaction, ectoplacental cone invaded by blood, extraembryonic ectoderm, embryonic axis visible, |
| 9b | | Early streak (ES), gastrulation starts, first evidence of mesoderm |
| 10a | 7 | Mid streak (MS), amniotic fold starts to form |
| 10b | | Late streak, no bud (LSOB), exocoelom |
| 10c | | Late streak, early bud (LSEB), allantoic bud first appears, node, amnion closing |
| 11a | 7.5 | Neural plate (NP), head process developing, amnion complete |
| 11b | | Late neural plate (LNP), elongated allantoic bud |
| 11c | | Early head fold (EHF) |
| 11d | | Late head fold (LHF), foregut invagination |
| 12a | 8 | 1-4 somites, allantois extends, 1st branchial arch, heart starts to form, foregut pocket visible, preotic sulcus at 2-3 somite stage) |
| 12b | | 5-7 somites, allantois contacts chorion at the end of TS12 Absent 2nd arch, >7 somites |
| 13 | 8.5 | Turning of the embryo, 1st branchial arch has maxillary and mandibular components, 2nd arch present Absent 3rd branchial arch |
| 14 | 9 | Formation & closure of ant. neuropore, otic pit indented but not closed, 3rd branchial arch visible Absent forelimb bud |
| 15 | 9.5 | Formation of post. neuropore, forelimb bud, forebrain vesicle subdivides Absent hindlimb bud, Rathke's pouch |
| 16 | 10 | Posterior neuropore closes, Formation of hindlimb & tail buds, lens plate, Rathke's pouch; the indented nasal processes start to form Absent thin & long tail |
| 17 | 10.5 | Deep lens indentation, adv. devel. of brain tube, tail elongates and thins, umbilical hernia starts to form Absent nasal pits |
| 18 | 11 | Closure of lens vesicle, nasal pits, cervical somites no longer visible Absent auditory hillocks, anterior footplate |
| 19 | 11.5 | Lens vesicle completely separated from the surface epithelium. Anterior, but no posterior, footplate. Auditory hillocks first visible Absent retinal pigmentation and sign of fingers |
| 20 | 12 | Earliest sign of fingers (splayed-out), posterior footplate apparent, retina pigmentation apparent, tongue well-defined, brain vesicles clear Absent 5 rows of whiskers, indented anterior footplate |
| 21 | 13 | Anterior footplate indented, elbow and wrist identifiable, 5 rows of whiskers, umbilical hernia now clearly apparent Absent hair follicles, fingers separate distally |
| 22 | 14 | Fingers separate distally, only indentations between digits of the posterior footplate, long bones of limbs present, hair follicles in pectoral, pelvic and trunk regions Absent open eyelids, hair follicles in cephalic region |
| 23 | 15 | Fingers & Toes separate, hair follicles also in cephalic region but not at periphery of vibrissae, eyelids open Absent nail primordia, fingers 2-5 parallel |
| 24 | 16 | Reposition of umbilical hernia, eyelids closing, fingers 2-5 are parallel, nail primordia visible on toes Absent wrinkled skin, fingers & toes joined together |
| 25 | 17 | Skin is wrinkled, eyelids are closed, umbilical hernia is gone Absent ear extending over auditory meatus, long whiskers |

TABLE 2-continued

Theiler Stages of Mouse Embryo Development

| Theiler Stage | dpc | (C57BLxCBA) F1 mice |
|---|---|---|
| 26 | 18 | Long whiskers, eyes barely visible through closed eyelids, ear covers auditory meatus |
| 27 | 19 | Newborn Mouse |
| 28 | | Postnatal development |
| Adult | | Adult Mouse |

Comparisons of Embryo Stages

At birth, the mouse contains the same differentiated cell types and tissues as a human even though the mouse pup is fully developed and born only 19 days following fertilization of the egg, compared to approximately 266 days for the human. For the initial 100 hours or so of post-fertilization development, however, the mouse and human embryos are virtually indistinguishable visually from one another. These similarities have been documented many times with correlations and comparisons being updated over the years.

Consequently, it is well established to one of skill that certain windows of development, or aligned development windows, between rodent (mouse and rat) and humans exist and that these windows provide an excellent correlation of developmental timing across species. As such, treatment windows identified in non-human species may be converted into a treatment window for human species. This is not dissimilar to the reliance placed on animal models in the prediction of efficacy in humans. Table 3 provides a comparison among Human, Mouse and Rat but other species have been examined and stages calculated.

TABLE 3

Multi-species Carnegie Stages (9-15)

| Species | Stage | 9 | 10 | 11 | 12 | 13 | 14 | 15 |
|---|---|---|---|---|---|---|---|---|
| Human | Days | 20 | 22 | 24 | 28 | 30 | 33 | 36 |
| Mouse | Days | 9 | 9.5 | 10 | 10.5 | 11 | 11.5 | 12 |
| Rat | Days | 10.5 | 11 | 11.5 | 12 | 12.5 | 13 | 13.5 |

TABLE 3b

Multi-species Carnegie Stages (16-23)

| Species | Stage | 16 | 17 | 18 | 19 | 20 | 21 | 22 | 23 |
|---|---|---|---|---|---|---|---|---|---|
| Human | Days | 40 | 42 | 44 | 48 | 52 | 54 | 55 | 58 |
| Mouse | Days | 12.5 | 13 | 13.5 | 14 | 14.5 | 15 | 15.5 | 16 |
| Rat | Days | 14 | 14.5 | 15 | 15.5 | 16 | 16.5 | 17 | 17.5 |

Other means of identifying treatment windows for human subjects includes the use of direct and/or indirect markers of development. In one embodiment of the invention, markers of gestational age can be used to determine the administration timing of EDI200. For example, after implantation, cells within the developing placenta (syncitiotrophoblasts) synthesize and secrete Human chorionic gonadotropin (hCG) into the maternal bloodstream. The main function of serum hCG is to maintain the corpus luteum in the maternal ovary and therefore maintain the early pregnancy. However, as can be seen from Table 4, hCG levels in the mother's serum provides an indication as to the gestational age range of the embryo or fetus. The table was adapted from the website of Dr. Mark Hill at the University of New South Wales (UNSW).

TABLE 4

Levels of hCG in serum

| Weeks after Last Menstrual period (LMP) | Days after Fertilization | hCG level (mIU/ml or IU/L) |
|---|---|---|
| Week 3 | 7 | 0 to 5 |
| Week 4 | 14 (next period due) | 5 to 426 |
| Week 5 | 21 | 18 to 7340 |
| Week 6 | 28 | 1,080 to 56,500 |
| Weeks 7 to 8 | 35 to 42 | 7,650 to 229,000 |
| Weeks 9 to 12 | 49 to 70 | 25,700 to 288,000 |
| Weeks 13 to 16 | 77 to 100 | 13,300 to 254,000 |
| Weeks 17 to 24 | | 4,060 to 165,400 |
| Weeks 25 to birth | | 3,640 to 117,000 |

From the table it is evident that measurements of hCG can inform a clinician as to the developmental stage of the embryo and hence the timing of administration of EDI200 can be determined to provide the optimal outcome for alteration of the phenotype.

Other means of determining the most appropriate therapeutic window of administration include methods such as those reviewed and described by O'Rahilly (O'Rahilly R, et al, Developmental Stages in Human Embryos: Revised and New Measurements. Cells Tissues Organs 2010; 192:73-84), the contents of which are incorporated herein in their entirety. In these methods, the greatest length or GL (GL; defined as the length of an embryo or a fetus exclusive of the lower limbs) was measured via ultrasound and correlated with days of gestation or Carnegie stage. Table 5 summarizes the findings of O'Rahilly. Therefore, in addition to Theiler and Carnegie charts, actual measurements may be made via ultrasound of the embryo or fetus and administration of EDI200 made at a time when it would afford the greatest therapeutic efficacy as taught by the present invention.

TABLE 5

Use of Greatest Length as Treatment Window Guide

| Stage | Greatest length range (mm) | Proposed Age (days) |
|---|---|---|
| 12 | 3.9-4.9 | 29-31 |
| 13 | 4.8-5.3 | 30-33 |
| 14 | 6.7-7.8 | 33-35 |
| 15 | 8.0-8.5 | 35-37 |
| 16 | 7.0-10.9 | 37-40 |
| 17 | 11.2-13.2 | 39-42 |
| 18 | 14.0-15.5 | 42-45 |
| 19 | 16.3-18.5 | 45-47 |
| 20 | 18.5-20.8 | 47-50 |
| 21 | 22.0-22.7 | 49-52 |
| 22 | 24.0-25.8 | 52-55 |
| 23 | 27.0-32.0 | 53-58 |

Treatment or development windows may also be defined as "during gestation", at a time related to maturity at birth, a time relative to time of independence, a time of appearance or completion of primary dentition or at permanent dentition. The comparative times are listed for mouse, dog and human in Table 6.

TABLE 6

Additional Treatment Windows

| Species | Gestation | Relative Maturity at Birth | Time to Independence | Primary Dentition | Permanent Dentition |
|---|---|---|---|---|---|
| Mouse | 20 d | 27 wks | 3 wks | None | 4 wks |
| Dog | 60 d | 36 wks | 6 wks | 12 wks | 28 wks |
| Human | 265 d | 40 wks | 18 yrs | 3 yrs | 12.5 yrs |

The invention is further illustrated by the following non-limiting examples.

EXAMPLES

Example 1. Mapping Tissue Responsiveness to EDI200

The TNF family ligand ectodysplasin A (EDA) and its receptor EDAR are required for proper development of skin appendages such as hair, teeth and eccrine sweat glands. "Loss of function" EDA mutations cause X-linked hypohidrotic ectodermal dysplasia (XLHED), a condition that can be ameliorated in mice and dogs by timely administration of recombinant EDA or EDI200.

In an effort to determine the temporal responsiveness to EDI200 as well as the intra-amniotic dose required and duration of EDI200 signaling necessary for the formation of any EDA-dependent structures such as ectodermal appendages, the following experiments were conducted.

Figure 1:
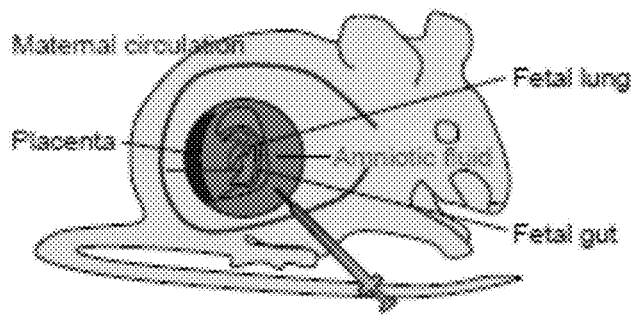
FIG. 1 is a diagram of the general intra-amniotic procedure of the experiments described herein. Two cohorts were studied at doses of 10 mg/kg and 100 mg/kg. Untreated siblings were also studied. In EDA-deficient organisms, endogenous EDA is either not made or inactive, but the EDA receptor remains expressed in signaling-competent form. Providing recombinant EDA in the form of EDI200 is sufficient to activate the EDAR signaling pathway and to rescue some or all of the EDA-deficient phenotype.

Two cohorts were studied at intra-amniotic doses of 10 mg/kg and 100 mg/kg. Untreated siblings were also studied. In EDA-deficient organisms, endogenous EDA is either not made or inactive, but the EDA receptor remains expressed in signaling-competent form. Providing recombinant EDA in the form of EDI200 is sufficient to activate the EDAR signaling pathway and to rescue substantially all of the EDA-deficient phenotype. FIG. 1 is a diagram of the general intra-amniotic procedure of the experiments described herein.

EDI200 was injected into amniotic sacs of pregnant wild-type mice to evaluate drug uptake and pharmacokinetics. Fetal and maternal serum levels were monitored.

Based on these results, EDI200 at doses of 10 or 100 mg/kg fetal weight was administered intra-amniotically to Tabby mouse fetuses at gestational age day 15 (E15). Three siblings were left untreated.

Fetal survival rates were determined and phenotypic correction following E15 intra-amniotic administration of EDI200 was assessed. The spectrum of hair, opthalmic, sweat gland and dentition responses to EDI200 was evaluated through adulthood.

Fertility of all treated mice was investigated by short-term mating with untreated animals. Ten of the eleven treated mice are being further evaluated until natural death.

Study Animals

Tabby mice and their wild type counterparts were used in the in vivo assessment of EDI200. The Tabby mouse strain was white-bellied agouti B6CBAa $A^{w-J}/A$-$Eda^{Ta}/J$ (000314; Jackson Laboratory) bred as $Eda^{Ta}/Eda^{Ta}$ and $Eda^{Ta}/Y$ mutants. The WT mouse strain was in the same genetic background bred as +/+ and +/Y controls.

The Tabby phenotype in mice was the result of Ectodysplasin-A1 deficiency (Srivastava et al. 1997). This mouse strain was the animal model of XLHED and was used for gene expression and EDI200 efficacy studies. Male and female animals were randomly assigned to test groups.

Birth dates were recorded and thereafter daily photographs were taken of the tail and eye. At weaning (day 21 postbirth), photographs were taken of the tail, of the tip of tail, of guard hair, of the retro-auricular region, and of the eye. A sweat test as described in PCT Publication WO 2010/113117 and its priority document the contents of each of which are incorporated herein by reference in their entirety was also performed. At day 30 postbirth, animals were sacrificed and skulls were collected and prepared and photographs were taken of the upper and lower molars.

Assessment of Phenotype Correction

The animals were visually assessed (live animals or isolated skulls or tissue sections) for correction of the Tabby phenotype concerning presence of sweat glands, molars, tail hair, hair behind ears, tail kink, and eye appearance.

Summary of findings. EDI200 injection led to a striking reversion to a normal phenotype. A dose-dependent correction was also observed for untreated siblings. The data are summarized in Table 7.

TABLE 7

| | Outcomes | | | | | | | |
|---|---|---|---|---|---|---|---|---|
| | Tail Hair | Tail Form | Hair behind ears | Guard Hair | Eyes | Teeth | Sweat Glands | Progeny after mating |
| EDI200, 100 mg/kg (n = 7) | 3 | 3 | 3 | 3 | 3 | n.a. | 3 | 7/7 |
| Untreated Siblings (n = 2) | 3 | 2.5 | 3 | 3 | 3 | n.a. | 3 | 2/2 |
| EDI200, 10 mg/kg (n = 4) | 3 | 3 | 3 | 3 | 3 | n.a. | 2.75 | 4/4 |
| Untreated Siblings (n = 2) | 2 | 3 | 3 | 2 | 2 | n.a. | 1 | 1/1 |

Figure 2:
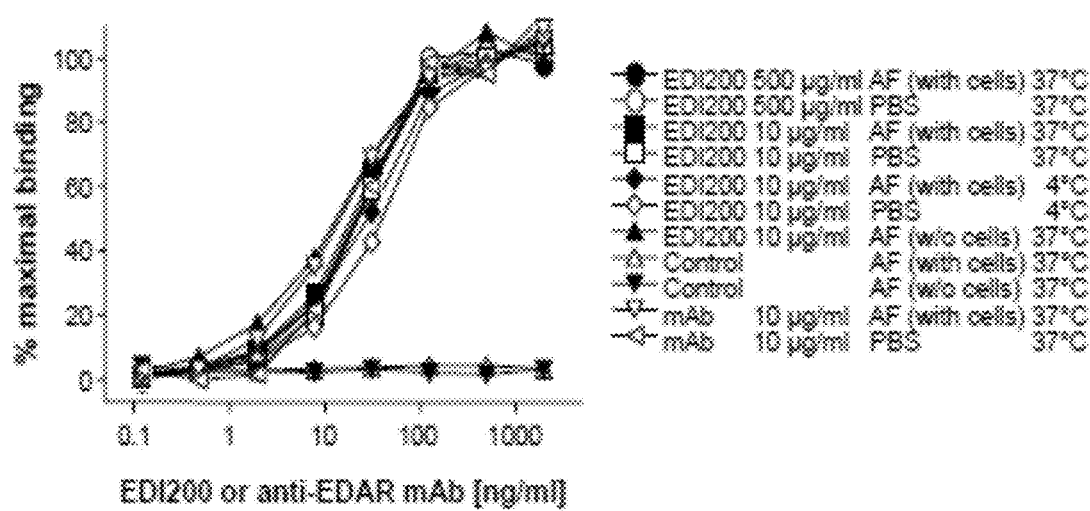
FIG. 2 is a plot of percent maximal receptor binding of EDI200 as a function of dose from 0.1 ng/mL to 1000 ng/mL as measured in a receptor binding ELISA. An anti-EDAR monoclonal antibody served as a positive control. EDI200 was stable in amniotic fluid (AF) at 37° C. for at least one week without detectable loss of activity. It is noted that the amniotic sac of an E15 mouse fetus (approximately 0.3 g body weight) contains on average 125 uL amniotic fluid.

According to the table, "3" is fully corrected, at least 90% relative to wild type; "2.75" is at least 85% corrected relative to wild type; "2.5" is at least 80% corrected relative to wild type; "2" is partially corrected, close to wild type, at least 75% relative to wild type; "1" is partially corrected, close to native Tabby mice, equal or less than 70% of wild type; "0" is no correction. "n.a." is not available Example 2. Stability in Amniotic Fluid EDI200 was demonstrated to be stable in amniotic fluid. The data are given in FIG. 2 and show a plot of percent maximal receptor binding of EDI200 as a function of dose from 0.1 ng/mL to 1000 ng/mL as measured in a receptor binding ELISA. An anti-EDAR monoclonal antibody served as a positive control. EDI200 was stable in amniotic fluid (AF) at 37° C. for at least one week without detectable loss of activity. It is noted that the amniotic sac of an E15 mouse fetus (approximately 0.3 g body weight) contains on average 125 uL amniotic fluid (AF).

Example 3. Serum Concentration

Figure 3:
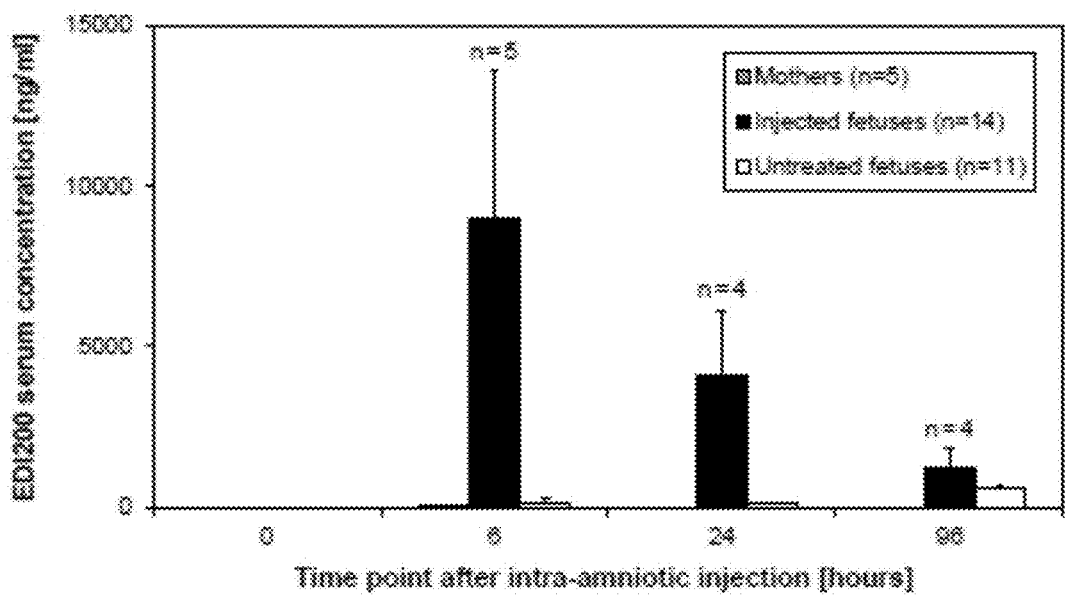
FIG. 3 is a histogram showing the concentration of EDI200 in serum in ng/mL as a function of time post intra-amniotic injection. In order, the treatment groups were: shaded bars (mothers), black bars (fetuses) and open bars (untreated fetuses). Intra-amniotic administration of EDI200 (100 mg/kg) to E15 wild-type mice resulted in substantial fetal uptake with mean serum levels of 9.0 ug/mL and 1.2 ug/mL at 6 and 96 hours, respectively. There was some leakage to the mother's circulation and to untreated siblings.

The concentration of EDI200 in fetal and mother serum was investigated. FIG. 3 is a histogram showing the concentration of EDI200 in serum in ng/mL as a function of time post intra-amniotic injection. In order, the treatment groups were: shaded bars (mothers), black bars (fetuses) and open bars (untreated fetuses). Intra-amniotic administration of EDI200 (100 mg/kg) to E15 wild-type mice resulted in substantial fetal uptake with mean serum levels of 9.0 ug/mL and 1.2 ug/mL at 6 and 96 hours, respectively. There was some leakage to the mother's circulation and to untreated siblings.

Example 4. Phenotypic Outcomes: Tail, Tail Hair and Eyes

Photographs were taken of both treated and untreated animals. The data are shown in FIG. 4. The panel of photographs taken of treated and untreated Tabby mice reveal that Tabby mouse fetuses treated with EDI200 were born without complications and showed normal weight gain and darker coat than untreated control animals and that eyes were more open hair was more plentiful in the retroauricular region; guard hair and tail hair were also normal; and tail tip was normal.

In contrast to a single maternal injection of EDI200 in Tabby mice at E15, which corrected the XLHED phenotype in offspring only partially, a single intra-amniotic dose of 10 mg/kg or above resulted in compete phenotypic correction. No adverse effects were observed. All treated Tabby mice showed normal behavior and fertility.

Example 5. Sweat Test

Hind paws were painted with a solution of 3% (w/v) iodine in ethanol. Once dry, the paws were painted with a suspension of 40% (w/v) of starch in mineral oil. Photos were taken one to two minutes later. The starch iodine test was determined to be positive when black dots were visible, indicative of the presence of liquid medium and consistent with the presence of sweat glands. The data are shown in FIG. 5 as a panel of photographs taken of wild-type, treated and untreated Tabby mice demonstrating that EDI200 restores the presence (Panel B) and function (Panel A) of sweat glands in the footpads of treated fetuses.

Example 6. Dentition

Photographs were taken of both treated and untreated animals. Shown in FIG. 6 is a panel of photographs taken of treated, untreated and wild type mice. The photographs illustrate that administration of EDI200 via intra-amniotic route at E15 reverses the Tabby tooth phenotype as evidenced by the clearly defined dentition of the molars.

The invention claimed is:

1. A method for altering one or more phenotypic presentations of ectodermal dysplasia in a mammalian organism diagnosed with or suspected of having ectodermal dysplasia comprising, administering to said mammalian organism a pharmaceutical composition comprising EDI200, wherein administration is via an intra-amniotic route and wherein the pharmaceutical composition is administered in a dose of between 1 mg/kg and 100 mg/kg of fetal weight.

2. The method of claim 1, wherein EDI200 is a protein hexamer of six identical species of a protein, each species comprising the amino acid sequence of SEQ ID NO.: 1.

3. The method of claim 1, wherein the ectodermal dysplasia is hypohidrotic ectodermal dysplasia.

4. The method of claim 3, wherein hypohidrotic ectodermal dysplasia is X-linked hypohidrotic ectodermal dysplasia (XLHED).

5. The method of claim 1, wherein intra-amniotic administration is effected via direct injection into the amniotic sac or via catheter infusion to the amniotic sac.

6. The method of claim 1, wherein the mammalian organism is a human fetus and wherein said pharmaceutical composition is administered at a time period during gestation selected from the group consisting of the second trimester and the third trimester of pregnancy.

7. The method of claim 6 wherein the phenotypic presentation is abnormal morphology or lack of sweat glands and administration is during the third trimester of pregnancy.

8. A method for treating hypohidrotic ectodermal dysplasia in a mammalian organism diagnosed with or suspected of having hypohidrotic ectodermal dysplasia comprising, administering to said mammalian organism an effective amount of a pharmaceutical composition comprising EDI200, wherein administration is via an intra-amniotic route and wherein the pharmaceutical composition is administered in a dose of between 1 mg/kg and 100 mg/kg of fetal weight.

9. The method of claim 8, wherein hypohidrotic ectodermal dysplasia is X-linked hypohidrotic ectodermal dysplasia (XLHED).

10. The method of claim 9, wherein the mammalian organism is a human fetus and wherein said pharmaceutical composition is administered via direct injection into the amniotic sac or via catheter infusion to the amniotic sac, at a time period during gestation selected from the group consisting of the second trimester and the third trimester of pregnancy.

* * * * *